United States Patent [19]

Ho

[11] Patent Number: 4,617,311

[45] Date of Patent: Oct. 14, 1986

[54] ANTIASTHMATIC METHOD

[75] Inventor: Peter P. K. Ho, Carmel, Ind.

[73] Assignee: Eli Lilly and Company, Indianapolis, Ind.

[21] Appl. No.: 736,896

[22] Filed: May 17, 1985

[51] Int. Cl.$^4$ ............................................. A61K 31/44
[52] U.S. Cl. .................................... 514/353; 514/826
[58] Field of Search ................................ 514/353, 826

[56] References Cited

U.S. PATENT DOCUMENTS

| | | | |
|---|---|---|---|
| 4,057,636 | 11/1977 | Petersen | 424/263 |
| 4,320,134 | 3/1982 | Iizuka et al. | 514/826 X |
| 4,347,250 | 8/1982 | Durant et al. | 514/353 X |
| 4,378,361 | 3/1983 | Schromm et al. | 514/826 X |
| 4,388,312 | 6/1983 | Terao et al. | 514/826 X |
| 4,409,222 | 10/1983 | Arrigoni-Martelli | 424/251 |

OTHER PUBLICATIONS

Petersen et al., "Synthesis and Hypotensive Activity of N-Alkyl-N''-Cyano-N'-Pyridylguanidines," *J. Med. Chem.*, 21(8), 773 (1978).

*Primary Examiner*—Leonard Schenkman
*Attorney, Agent, or Firm*—Robert A. Conrad

[57] ABSTRACT

This invention provides a method of treating asthma in mammals which comprises administering an effective amount of Pinacidil.

4 Claims, No Drawings

ANTIASTHMATIC METHOD

BACKGROUND OF THE INVENTION

Pinacidil (N''-cyano-N-4-pyridinyl-N'-(1,2,2-trimethylpropyl)guanidine monohydrate) is a potent antihypertensive agent of low toxicity. See, e.g. U.S. Pat. No. 4,057,636, Example 47. This compound is currently being evaluated clinically for the management of hypertension.

This invention relates to the discovery that Pinacidil is also a potent bronchodilating agent useful in the treatment of asthma in mammals.

SUMMARY OF THE INVENTION

This invention provides a method of treating mammals suffering from or susceptible to asthma which comprises administering to said mammal an effective amount of Pinacidil.

DETAILED DESCRIPTION OF THE PREFERRED EMBODIMENTS

Pinacidil is taught as Example 47 in U.S. Pat. No. 4,057,636. See also U.S. Pat. No. 4,409,222 and Petersen et al., *J. Med. Chem.*, 21 (8), 773 (1978). When used herein, the term "Pinacidil" refers to the free base of N''-cyano-N-4-pyridinyl-N'-(1,2,2-trimethylpropyl)-guanidine and any pharmaceutically acceptable solvates and/or pharmaceutically acceptable acid addition salts thereof. Such solvates include those from non-toxic solvents such as water or ethanol.

However, the preferred compound as used in the method of the present invention is that of the monohydrate of the free base form of Pinacidil.

As used in the method of this invention, Pinacidil may be administered by various routes including the oral, rectal, transdermal, subcutaneous, intravenous, intramuscular, inhalation, insufflation, or intranasal routes, being usually employed in the form of a pharmaceutical composition. Such compositions are prepared in a manner well known in the pharmaceutical art and comprise Pinacidil associated with a pharmaceutically acceptable carrier.

The compositions are preferably formulated in a unit dosage form, each dosage containing from about 5 to about 500 mg, more usually about 25 to about 300 mg, of the active ingredient. The term "unit dosage form" refers to physically discrecte units suitable as unitary dosages for human subjects and other mammals, each unit containing a predetermined quantity of Pinacidil calculated to produce the desired therapeutic effect, in association with the required pharmaceutical carrier.

Pinacidil is effective over a wide dosage range. For example, dosages per day will normally fall within the range of about 0.5 to about 300 mg/kg of body weight. In the treatment of adult humans, the range of about 1 to about 50 mg/kg, in single or divided doses, is preferred. However, it will be understood that the amount of Pinacidil actually administered will be determined by a physician, in the light of the relevant circumstances including the condition to be treated, the chosen route of administration, the age, weight, and response of the individual patient, and the severity of the patient's symptoms, and therefore the above dosage ranges are not intended to limit the scope of the invention in any way.

I have discovered that Pinacidil is a potent bronchodilator and is useful in blocking anaphylactic responses, thereby making the compound useful in treating mammals suffering from or susceptible to asthma. This biological activity was demonstrated in the following test system.

Following the general procedure taught by Andersson, *Brit. J. Pharmacol.*, 69, 467 (1980), mixed sex Hartley strain guinea pigs (250–300 g) were sensitized to ovalbumin by a single injection of 1 mcg of ovalbumin mixed with 50 mg of aluminum hydroxide per animal. These animals were used 21 to 26 days later for aerosol challenge with ovalbumin.

Groups of five guinea pigs were treated with Pinacidil, hydralazine, theophylline, or placebo (vehicle only) two hours prior to the aerosol challenge. All the animals also received 3 mg/kg pyrillamine orally two hours prior to the aerosol challenge in order to blunt the histamine component of the anaphylaxis. The compounds were administered orally as a suspension in 10% acacia.

Anaphylaxis was induced by exposure to an aerosol of 10 mg of ovalbumin per milliliter of water for 10 minutes delivered by a Tri-R venturi nebulizer, particle size 2 to 5 micron diameter, at a delivery rate of 0.4 ml of solution per minute. The guinea pigs were placed in specially constructed chambers for exposure to the aerosol. The aerosol was introduced from the bottom of the chamber and exhausted from the top. A baffle above the chamber inlet port provided even distribution of the aerosol throughout the chamber. The animals were supported above the inlet on a wire mesh disk. The chamber was under slight negative pressure to enhance the exhaust of the aerosol which was passed through a calcium chloride trap followed by a super-cooled condenser trap.

Throughout the 10 minute period of aerosol challenge, the animals were observed for the symptomology of convulsive cough, convulsive collapse, and death as reported by Herxhermer, *J. Physiology*, 117, 251 (1952). The number of animals that responded to the aerosol challenge for each of the above parameters as well as the time for the response to occur were recorded. The data were analyzed by comparing the severity index (the sum of the number of animals that coughed, collapsed, and/or died) between the treated and placebo group of guinea pigs. Thus, the maximum severity index for each group of five guinea pigs is 15. On the average, the severity index for the placebo group was 9–12. The percent inhibition of anaphylaxis was determined by the following formula:

$$\text{Percent inhibition} = \left[1 - \frac{S_d}{S_p}\right] \times 100$$

where $S_d$ is the severity index for the drug treated animals and $S_p$ is the severity index of the placebo treated animals. The results of these experiments are summarized in Table 1. Each result represents the average of 1–3 experiments.

TABLE 1

| Inhibition of Antigen-Induced Anaphylaxis in Guinea Pigs | | | |
|---|---|---|---|
| Compound | Dose mg/kg p.o. | Severity Index | Percent Inhibition |
| Placebo (vehicle only) | — | 9.0 | — |
| Theophylline | 50 | 2.7 | 70.7%* |
| Pinacidil | 30 | 0.7 | 92.7%* |

TABLE 1-continued

Inhibition of Antigen-Induced Anaphylaxis in Guinea Pigs

| Compound | Dose mg/kg p.o. | Severity Index | Percent Inhibition |
| --- | --- | --- | --- |
| Pinacidil | 10 | 1.0 | 89%* |
| Pinacidil | 3 | 4.3 | 52%* |
| Pinacidil | 1 | 7.5 | 16.5% |
| Hydralazine | 30 | 6.0 | 33% |
| Hydralazine | 10 | 8.5 | 14% |
| Hydralazine | 3 | 9.0 | 0% |

*Statistically different from placebo, $p < 0.05$.

I claim:

1. A method of treating mammals suffering from or susceptible to asthma which comprises administering an effective amount of Pinacidil.

2. The method of claim 1 wherein Pinacidil is administered orally or by inhalation.

3. The method of claim 2 wherein about 0.5 to about 300 mg/kg of Pinacidil is administered.

4. The method of claim 3 wherein about 1 to about 50 mg/kg of Pinacidil is administered.

* * * * *